United States Patent [19]

Aungst et al.

[11] Patent Number: 4,673,679

[45] Date of Patent: Jun. 16, 1987

[54] USE OF PRODRUGS OF 3-HYDROXYMORPHINANS TO PREVENT BITTER TASTE UPON BUCCAL, NASAL OR SUBLINGUAL ADMINISTRATION

[75] Inventors: Bruce J. Aungst; Munir A. Hussain, both of Wilmington, Del.

[73] Assignee: E. I. Du Pont de Nemours and Company, Wilmington, Del.

[21] Appl. No.: 863,045

[22] Filed: May 14, 1986

[51] Int. Cl.$^4$ .............................................. A61K 31/44
[52] U.S. Cl. ................................. 514/282; 514/812; 514/969
[58] Field of Search ...................... 514/969, 282, 812

[56] References Cited

U.S. PATENT DOCUMENTS 4,464,378 8/1984 Hussain ............................... 514/282
4,582,835 4/1986 Lewis et al. ........................ 514/282

Primary Examiner—Stanley J. Friedman

[57] ABSTRACT

Aliphatic, aromatic, carbonate, carbamate, or sulfonate ester prodrugs of 3-hydroxymorphinans lack the bitter taste of the parent compounds and provide enhanced bioavailability of 3-hydroxymorphinans from buccal, nasal, and sublingual dosage forms.

8 Claims, No Drawings

USE OF PRODRUGS OF 3-HYDROXYMORPHINANS TO PREVENT BITTER TASTE UPON BUCCAL, NASAL OR SUBLINGUAL ADMINISTRATION

BACKGROUND OF THE INVENTION

This invention relates to pharmaceutical compositions containing opioids and opioid antagonists, in particular, prodrugs of 3-hydroxymorphinans, suitable for buccal, nasal or sublingual administration and methods of using prodrugs of 3-hydroxymorphinans for buccal, nasal or sublingual administration.

The oral administration of many 3-hydroxymorphinans including nalbuphine, naltrexone, naloxone, nalmefene, morphine, butorphanol, oxymorphone, hydromorphone, levorphanol, levallorphan, buprenorphine and etorphine, will elicit a substantially lesser response as compared to an equal dosage administered parenterally. This reduction in potency most commonly results from the extensive metabolism of the drug during its transit from the gastrointestinal tract to the general circulation. For example, the liver and intestinal mucosa, through which an orally administered drug passes before it enters the circulatory system, are very active enzymatically and can thus metabolize the drug in many ways.

When an orally administered drug is metabolized rapidly by the gastrointestinal system or liver prior to entering the general circulation, its bioavailability is low. This problem can be circumvented by administering the drug by another route. Examples of such alternative routes include buccal, nasal or sublingual. Drugs administered by these routes avoid hepatic and gut-wall metabolism, resulting in increased bioavailability and potency compared to oral administration.

Although 3-hydroxymorphinans are well absorbed from the buccal cavity, many of these compounds have a bitter taste which makes them difficult to administer by that route. The present invention relates to prodrugs of 3-hydroxymorphinans which are devoid of any taste, and are thus more suitable for buccal, sublingual, or nasal administration. Either rapid absorption and decline of plasma drug concentrations or prolonged plasma concentrations of active drug can be achieved by selecting prodrugs with appropriate solubility and hydrolysis rates. These can be formulated as tablets, gels, pastes, patches, or lozenges.

Several 3-hydroxymorphinans having various substituents on the nitrogen atom have been found to exhibit narcotic antagonist as well as narcotic analgesic activity. Such compounds are referred to as agonist-antagonists. Pachter and Matossian in U.S. Pat. No. 3,393,197, issued July 16, 1968, disclose N-substituted-14-hydroxydihydronormorphines, including the N-cyclobutylmethyl derivative, commonly called nalbuphine. Monkovik and Thomas, U.S. Pat. No. 3,775,414, disclose N-cyclobutylmethyl-3,14-dihydroxymorphinan, commonly called butorphanol. Bentley et al., U.S. Pat. No. 3,433,791, disclose 17-(cyclopropylmethyl)-α-(1,1-dimethylethyl)4,5-epoxy-18,19-dihydro-3-hydroxy-6-methoxy-α-methyl-6,14-ethenomorphinan-7-methanol, commonly called buprenorphine.

Still other N-substituted morphinan derivatives are pure narcotic antagonists with little or no agonist activity. Lewenstein, in U.S. Pat. No. 3,254,088, issued May 31, 1966, discloses N-allyl-7,8-dihydro-14-hydroxynormorphinone, commonly known as naloxone. Blumberg, Pachter, and Matossian, in U.S. Pat. No. 3,332,950, issued July 25, 1967, disclose N-substituted-14-hydroxydihydronormorphinones, including the N-cyclopropylmethyl analog, commonly known as naltrexone.

Morphine, oxymorphone, hydromorphone and levorphanol are well known 3-hydroxymorphinan analgesics.

A number of references disclose buccal, sublingual or nasal administration of opioids. G. F. Blane et al., in *Internatinal Conference on Radioactive Isotopes in Pharmacology*, 1969, disclose the absorption of etorphine and dihydromorphine from the buccal cavity. M. D. D. Bell et al., in *The Lancet*, 1 (8420), 71-73, 1985 disclose buccal administration of morphine sulfate. R. S. Todd in GB 2,100,985, published Jan. 12, 1983, discloses a pharmaceutical composition for the sublingual administration of buprenorphine and salts thereof. H. Lowey in U.S. Pat. No. 4,259,314, issued Mar. 31, 1981, discloses a lozenge for buccal administration containing dextromethorphan. A. A. Hussain in U.S. Pat. No. 4,464,378, issued Aug. 7, 1984, discloses a method of intranasal administration of narcotic antagonists and analgesics, including naloxone, naltrexone, nalbuphine, levorphanol, buprenorphine, and butorphanol, and novel dosage forms containing those compounds which are adapted for nasal administration.

A number of other references disclose formulations and delivery systems for buccal administration, including R. Cournut and G. Gaussens in U.S. Pat. No. 4,020,558, issued May 3, 1977; W. R. Porter in U.S. Pat. No. 4,229,447, issued Oct. 21, 1980; A. G. Tsuk in U.S. Pat. No. 3,972,995 issued Aug. 3, 1976, H. Lowey and H. H. Stafford in U.S. Pat. No. 3,870,790 issued Mar. 11, 1975, H. S. Russell in U.S. Pat. No. 3,444,858 issued May 20, 1969, A. Halpern and C. H. Bradney in U.S. Pat. No. 2,698,822 issued Jan. 4, 1955, L. Geller et al., in U.S. Pat. No. 3,632,743 issued Jan. 4, 1972 and T. Kissel and R. Bergauer in UK patent application GB 2,108,841A published May 25, 1983.

A. A. Hussain in U.S. Pat. No. 4,315,925, issued Feb. 16, 1982 discloses nasal administration of natural female sex hormones.

Bender et al., in U.S. Pat. No. 4,539,315, issued Sept. 3, 1985, disclose an aspirin composition for sublingual administration. A. F. Libby in U.S. Pat. No. 4,432,975 issued Feb. 21, 1984 discloses a microlozenge containing vitamin B-12 for sublingual administration.

SUMMARY OF THE INVENTION

According to the present invention there are provided pharmaceutical compositions consisting essentially of a therapeutically effective amount of a 3-hydroxymorphinan analgesic, agonist-antagonist, or narcotic antagonist, particularly those of formulas (I) and (II):

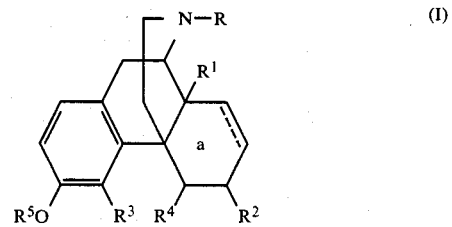

-continued

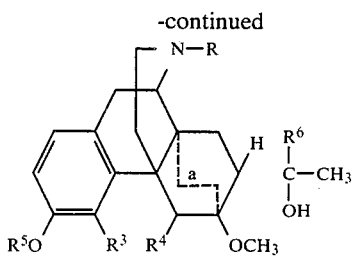
(II)

or their pharmaceutically acceptable acid addition salts, wherein:

a is a single bond, or double bond;

R is methyl, allyl, methylallyl, cyclopropylmethyl, or cyclobutylmethyl;

$R^1$ is hydrogen, or OH;

$R^2$ is hydrogen, OH, =O, or =CH$_2$;

$R^3$ and $R^4$ are H, or taken together are ———O———;

$R^5$ is alkanoyl of 2 through 18 carbon atoms; alkenoyl of 2 through 18 carbon atoms; mono- or dialkyl carbamoyl where each alkyl group contains 1 through 18 carbon atoms; alkylsulfonyl of 1 through 18 carbon atoms; alkylcarbonates where the alkyl group contains 1 through 18 carbon atoms; benzoyl, phenylsulfonyl; phenylcarbamoyl; substituted benzoyl, where the benzene ring contains 1 to 2 substituents individually selected from alkyl of 1 through 12 carbon atoms, $OR^7$, $NHR^7$ and $NR^7R^8$, Cl, F, Br, I, trifluoromethyl; substituted phenylsulfonyl or phenylcarbamoyl, where the benzene ring contains 1 to 2 substituents individually selected from alkyl of 1 through 12 carbon atoms, alkoxy of 1 through 12 carbon atoms, Cl, F, Br, I, $CF_3$;

$R^6$ is t-butyl or n-propyl;

$R^7$ is H, alkyl of 1 to 4 carbon atoms or $COR^9$;

$R^8$ is alkyl of 1 to 4 carbon atoms or $COR^9$; and $R^9$ is H, or alkyl of 1 to 4 carbon atoms;

and a pharmaceutically acceptable carrier suitable for buccal, nasal, or sublingual administration. Of particular interest are pharmaceutical compositions wherein the 3-hydroxymorphinan analgesic, agonist-antagonist, or narcotic antagonist is selected from the group consisting of nalbuphine, naltrexone, naloxone, nalmefene, morphine, butorphanol, oxymorphone, hydromorphone, levorphanol, levallorphan, buprenorphine and etorphine. More preferred are pharmaceutical compositions wherein the 3-hydroxymorphinan agonist-antagonist or narcotic antagonist is nalbuphine, naltrexone or naloxone.

Further provided is a method of treating pain, controlling appetite or reversing the effects of a narcotic drug in a mammal comprising, administering to the mammal buccally, nasally or sublingually a therapeutically effective amount of a 3-hydroxymorphinan prodrug selected from the groups described above.

Although generally classified as either a narcotic analgesic, an agonist-antagonist, or a narcotic antagonist, the 3-hydroxymorphinan compounds of this invention have other therapeutic utilities for which the buccal, nasal, and sublingual dosage forms of the invention may be very useful. For example, morphine has useful sedative and antitussive properties as well as being a valuable analgesic. Hydromorphone is a useful antitussive as well as a potent analgesic. Certain narcotic antagonists and agonist-antagonists, for example naloxone, naltrexone, and nalmefene may be useful as appetite suppressants. Naloxone also has utility as an antidiarrheal, and for treatment of gastrointestinal disorders such as irritable bowel syndrome. Naloxone may be useful in treating male impotency, and since it lowers prolactin levels in males, it may also be beneficial in treating certain gynecological disorders, including infertility and menstrual and menopausal disorders. Naloxone has also been reported to reverse certain neurological deficits caused by anoxia, hemorrhage, aging (manifested by decreased cognition, alertness, etc.) and other pathological processes, and may speed healing once such processes have begun. Naloxone has also shown therapeutic activity in treating certain psychiatric disorders (hallucinations of schizophrenia) and chronic alcoholism. It also is said to exhibit antipruritic activity.

As used herein:

Naloxone means (−)-17-Allyl-4,5α-epoxy-3,14-dihydroxymorphinan-6-one, or a salt thereof.

Naltrexone means (−)-17-(Cyclopropylmethyl)-4,5α-epoxy-3,14-dihydroxymorphinan-6-one, or a salt thereof.

Nalbuphine means (−)-17-(Cyclobutylmethyl)-4,5α-epoxymorphinan-3,6α,14-triol, or a salt thereof.

Nalmefene means 6-Desoxo-6-methylene-naltrexone, or a salt thereof.

Butorphanol means (−)-17-(Cyclobutylmethyl)-morphinan-3,14-diol, or a salt thereof.

Buprenorphine means (−)-17-(Cyclopropylmethyl)-α-(1,1-dimethylethyl)-4,5-epoxy-18,19-dihydro-3-hydroxy-6-methoxy-α-methyl-6,14-ethenomorphinan-7-methanol, or a salt thereof.

Oxymorphone means (−)-4,5α-Epoxy-3,14-dihyroxy-17-methylmorphinan-6-one, or a salt thereof.

Morphine means (−)-7,8-Didehydro-4,5α-Epoxy-17-methylmorphinan-3,6α-diol, or a salt thereof.

Hydromorphone means (−)-4,5α-Epoxy-3-hydroxy-17-methylmorphinan-6-one, or a salt thereof.

Levorphanol means (−)-17-Methylmorphinan-3-ol, or a salt thereof.

Levallorphan means (−)-17-(allyl)-morphinan-3-ol or a salt thereof.

Etorphine means (−)-4,5α-Epoxy-3-hydroxy-6-methoxy-α,17-dimethyl-α-propyl-6,14-ethenomorphinan-7α-methanol, or a salt thereof.

As noted above, reference to the 3-hydroxymorphinan prodrugs of this invention includes the pharmaceutically acceptable acid addition salts thereof. By the term "pharmaceutically acceptable acid addition salt" is meant any non-toxic pharmaceutically suitable salt of a compound described above which has the desired pharmacologic properties in mammals. Preparation of such salts is well known to thise skilled in pharmaceutical science. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate and pamoate.

DETAILED DESCRIPTION OF THE INVENTION

The synthesis of aliphatic, aromatic, carbonate, carbamate, and sulfonate esters of 3-hydroxymorphinans is described in U.S. pending application Ser. No. 733,464 filed May 14, 1985, in EPO Published Application No. 0170090, published Feb. 6, 1986, and in German Pat. No. DE 2,323,192 issued to Lachmann et al., on Dec.

13, 1973, the disclosure of which is incorporated herein by reference. The preferred derivatives are those which are stable in the fluids of the mouth and nose, are well absorbed through the mucosal membranes, and are rapidly metabolized to the active drug after absorption into the systemic circulation.

Synthesis

The compounds of Formula (I) or Formula (II) of the present invention may be prepared by contacting a 3-hydroxymorphinan with an appropriate reagent such as an acylating or sulfonating agent in the presence of a catalyst. The starting reagents and catalysts used to make the compounds of Formula (I) and Formula (II) are known.

The methods described hereinafter are set forth with respect to the compounds of Formula (I). However, it will be clear to one skilled in the art that these methods can also be used to prepare compounds of Formula (II).

Compounds of Formula I wherein $R^5$ is alkanoyl, alkenoyl, or benzoyl are prepared by reacting the corresponding 3-hydroxymorphinan with one mole of an appropriate acid chloride, anhydride, or mixed anhydride in an aprotic solvent, in the presence of an acid acceptor such as an alkali metal or alkaline earth metal carbonate or bicarbonate or a tertiary amine such as pyridine or triethylamine. A solution of the acylating agent in the reaction solvent is added to a solution of a 3-hydroxymorphinan in the reaction solvent containing the base at a temperature ranging from 0° C. to the boiling point of the solvent, generally from 0° C. to room temperature being preferred. The reactants are kept in contact from 0.5 to 24 hours, generally 5 to 20 hours.

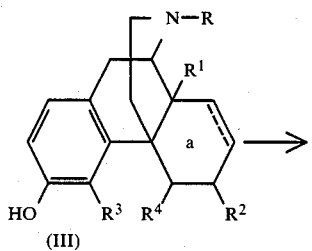

(III)

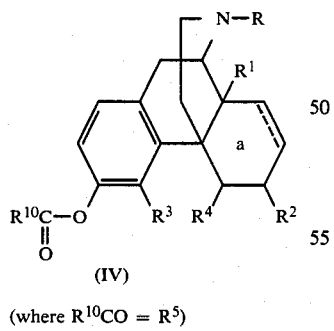

(IV)

(where $R^{10}CO = R^5$)

Likewise the alkylcarbonates are prepared by reacting the corresponding 3-hydroxymorphinan with a chloroformate of formula $R^5OCOCl$ in the presence of an acid acceptor to afford a compound of Formula IV, wherein $R^{10}$ is an alkoxy group.

Alternatively, compounds of Formula (I) wherein $R^5$ is alkanoyl or benzoyl may be prepared by treating a 3-hydroxymorphinan of Formula (III) with an acid in the presence of a dehydrating agent such as a carbodiimide, for example, dicyclohexylcarbodiimide. During the reaction the dicyclohexylcarbodiimide is converted to dicyclohexylurea. The reaction is generally run in the presence of a catalyst such as 4-dimethylaminopyridine, 4-pyrrolidinopyridine or 4-piperidinopyridine in an aprotic solvent such as toluene, methylene chloride, tetrahydrofuran or 1,2-dimethoxyethane. Generally, the reaction is run as follows: A compound of Formula (III) is added to a solution of the acid and the catalyst in an aprotic solvent and the reagents are allowed to react from 1–48 hours at a temperature of 0° C. to the boiling point of the solvent.

(III) + $R^5CO_2H$ +

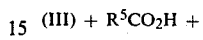

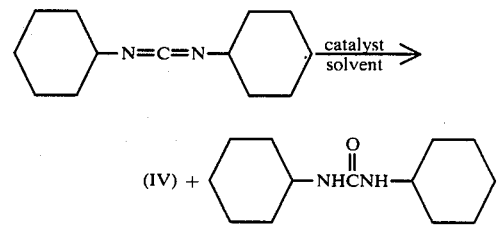

Substituted benzoates of Formula (VI) wherein the benzene ring is substituted with 2-$NHR^7$ can also be prepared by reaction of a 3-hydroxymorphinan of Formula (III) with an isatoic anhydride. A compound of Formula (III) is dissolved in a dipolar aprotic solvent such as N,N-dimethylformamide (DMF), dimethylsulfoxide (DMSO), N,N-dimethylacetamide (DMAC) or N-methylpyrrolidinone or tripyrrolinophosphine oxide. An isatoic anhydride (V) is added followed by a catalyst such as those described above and the solution is heated at 50°–150° C. for one to five hours under nitrogen.

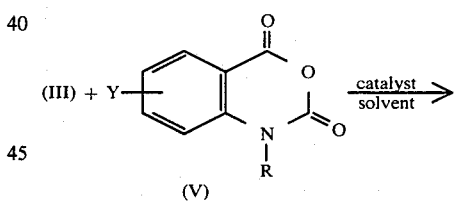

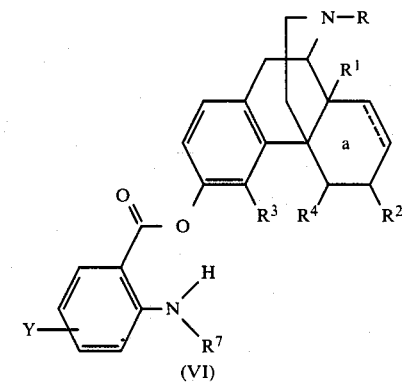

(VI)

where Y=H, $OR^7$, $NHR^7$, $NR^7R^8$, alkyl of 1 through 12 carbon atoms, Cl, F, Br, I, $CF_3$.

The method shown below is preferred for the preparation of an amino substituted benzoate of Formula (VIII) which may be additionally substituted with a Y group where Y is $OR^7$, $NR^7R^8$ wherein $R^7$ and $R^8$ are individually $C_1$–$C_4$ alkyl or $COR^9$, alkyl of 1 through 12 carbon atoms or trifluoromethyl.

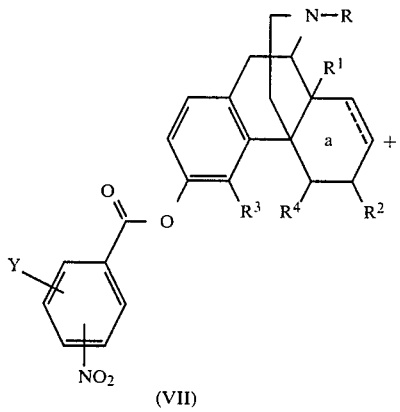

(VII)

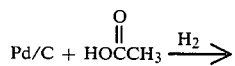

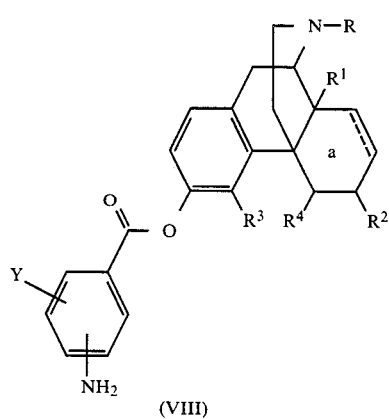

(VIII)

The 3-hydroxymorphinan nitrobenzoates of Formula (VII) except compounds where a is a double bond, may be hydrogenated to aminobenzoates (VIII) in a solvent such as methanol, ethanol or acetic acid, or in a mixture of an alcohol plus 5 to 10% acetic acid. The catalyst utilized may be 5 to 10% palladium on carbon or alumina, rhodium on carbon or alumina, or 5 to 10% platinum on carbon. Hydrogenation is conducted under hydrogen at atmospheric pressure to 60 psi at room temperature for one to six hours. If Raney nickel is used as the catalyst, a higher pressure, such as 100 to 1000 psi is utilized at a temperature from room temperature to 100° C. for five to 24 hours.

In compounds where a is a double bond, an alternate method of reduction (other than catalytic hydrogenation) must be employed so as not to reduce the double bond. The nitro group may be reduced with a metal such as iron or tin chloride in a protic solvent such as aqueous hydrochloric acid. Alternatively, reduction of the nitro group can be carried out with a mixture of sodium borohydride and a transition metal salt as catalyst, such as cobalt (II) chloride.

The requisite 3-hydroxymorphinan nitrobenzoates may be prepared by reaction of the compounds of Formula (III) with a nitrobenzoyl chloride or by reaction with nitrobenzoic acid in the presence of a coupling reagent as previously described. The nitro benzoyl chloride and nitrobenzoic acid starting reagents used to produce the nitrobenzoates are known.

Compounds of Formula I wherein $R^5$ is monoalkylcarbamoyl or phenylcarbamoyl are prepared by reacting the corresponding 3-hydroxymorphinan with one mole of an appropriate isocyanate, $R^{11}NCO$, where $R^{11}$ is alkyl of 1 through 18 carbon atoms or substituted or unsubstituted phenyl:

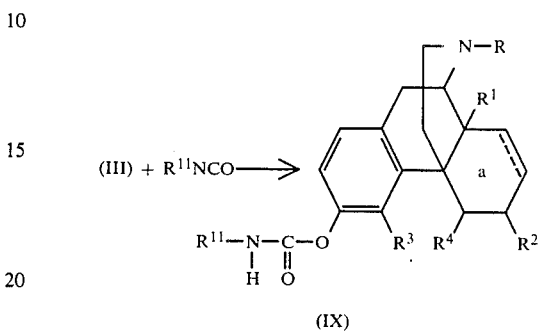

(IX)

Compounds of Formula I wherein $R^5$ is dialkylcarbamoyl are prepared by reacting the corresponding 3-hydroxymorphinan with one mole of an appropriate dialkylcarbamoyl chloride, $(R^{12})_2NCOCl$, where $R^{12}$ is alkyl of 1 through 18 carbon atoms.

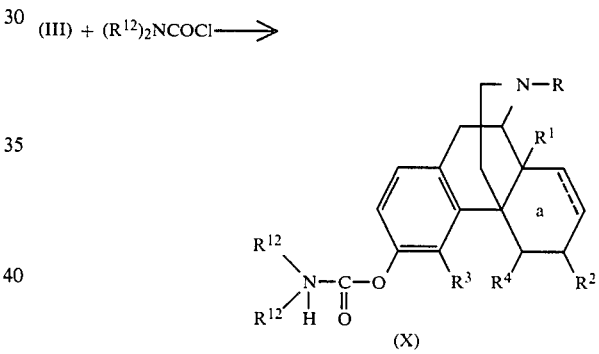

(X)

Compounds of Formula I wherein $R^1$ is alkylsulfonyl or phenylsulfonyl are prepared by reacting the corresponding 3-hydroxymorphinan with one mole of an appropriate sulfonyl chloride, $R^{13}SO_2Cl$, where $R^{13}$ is alkyl of 1 through 18 carbon atoms or substituted or unsubstituted phenyl:

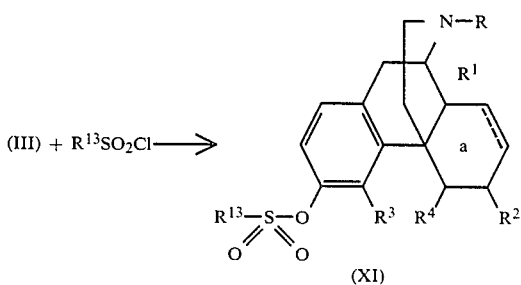

(XI)

Dosage and Dosage Forms

The 3-hydroxymorphinan prodrugs of the instant invention can be administered buccally, nasally, or sublingually to treat pain, to reverse the effects of narcotic drugs, or to achieve the other therapeutic effects discussed above using any pharmaceutically suitable formulation that results in the active agent reaching the agent's site of action in the body of a mammal. They can be administered either as individual agents or in combination with other therapeutic agents. Although these drugs can be administered alone, they are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of prodrug can be about 0.1 to 50 milligrams per kilogram of body weight. Ordinarily, when the more potent compounds of this invention are used, 0.1 to 20 milligrams per kilogram per day, given in divided doses 2 to 4 times a day or in sustained release form, is effective to obtain desired results.

Dosage forms (compositions) suitable for internal administration generally contain from about 0.5 to 500 milligrams of prodrug per unit. In these pharmaceutical compositions the 3-hydroxymorphinan prodrug will ordinarily be present in an amount of about 0.5 to 95% by weight based on the total weight of the composition.

Pharmaceutical dosage forms suitable for buccal, nasal or sublingual administration include tablets, gels, pastes, patches or lozenges. Suitable nontoxic pharmaceutically acceptable nasal carriers for use in the compositions of the present invention can be found in Remington's Pharmaceutical Sciences, 17th Edition, 1985. Lozenges for buccal or sublingual administration are described in Modern Pharmaceutics, edited by G. S. Banker and C. T. Rhodes.

Buccal patches can be prepared by mixing a suitable quantity of 3-hydroxymorphinan prodrug together with suitable quantities of hydroxypropyl cellulose (Klucel-®EF, Hercules Inc., Wilmington, DE), carboxypolymethylene (Carbopol® 934P, B. F. Goodrich Inc.), and polyethylene glycol (PEG) 400. The dry powders are triturated in a mortar and pestle. After forming a uniform mixture, PEG 400 is added and levigated with the dry mixture. The resulting composition is then pressed in a hydraulic press. Patches oval in shape are then cut to contain a suitable amount of a prodrug of a 3-hydroxymorphinan.

EXAMPLES

Nalbuphine-3-Pivalate Buccal Patch

A buccal patch of nalbuphine-3-pivalate HCl was prepared containing the following percentages by weight:

| | |
|---|---|
| nalbuphine-3-pivalate HCl | 18% |
| Klucel ®EF | 73.2% |
| Carbopol ® 934P | 5.4% |
| PEG 400 | 3.4% |

The first three ingredients are dry powders which were triturated in a mortar and pestle. After forming a uniform mixture, the PEG 400 was added and levigated with the dry mixture. The resulting composition was then pressed in a hydraulic press at 200° F. under 10,000 psi for 3 minutes. Oval patches were cut measuring 2.2×3.7 cm minor and major diameters and 0.04 cm thickness. These contained 36 mg of nalbuphine-3-pivalate HCl.

Nalbuphine-3-Acetyl Salicylate Buccal Patch

A buccal patch of nalbuphine-3-acetyl salicylate was prepared containing the following percentages by weight;

| | |
|---|---|
| nalbuphine-3-acetyl salicylate | 20% |
| Klucel ®EF | 66.71% |
| Carbopol ® 934P | 5.03% |
| Citric acid monohydrate | 5% |
| PEG 400 | 3.26% |

The first four ingredients listed above are dry powders which were triturated in a mortar and pestle. After forming a uniform mixture, the PEG 400 was added and levigated with the dry mixture. The resulting composition was then pressed in a hydraulic press at 200° F. under 10,000 psi for 3 minutes. Oval patches were cut measuring 2.2×3.7 cm minor and major diameters and 0.04 cm thickness. These contained 40 mg nalbuphine-3-acetyl salicylate.

Experimental

Among the experiments used to evaluate the prodrugs of the instant invention were measurements of their hydrolysis rates in rat and human plasma; bioavailability in rats and dogs administered oral and buccal doses of the drug or prodrug, and taste analysis. Parent drug concentration was determined using high pressure liquid chromatography analytical procedures which measure drug concentrations by electrochemical detection.

Taste Analysis

Parent drug and prodrugs were tasted. Results are shown in Tables 1–6. Nalbuphine, naloxone, naltrexone, oxymorphone, butorphanol and levallorphan taste bitter, whereas derivatives esterified in the 3-position are devoid of taste.

Plasma Hydrolysis

Prodrug was added to fresh plasma (less than 24 hours after withdrawal) to a concentration of 0.28 $\mu$M, incubated at 37° C. and the rate of parent drug appearance was measured. Results are shown in Table 1.

Oral and Buccal Drug Bioavailability

Rats and dogs were administered the parent drug intravenously (IV) or orally (PO). The doses were administered as aqueous solutions. Prodrugs were administered buccally (B). For buccal dosing in rats the esophagus was ligated under anesthesia to prevent swallowing of the dose solution. Prodrugs were applied in aqueous solution between the cheek and gum with a blunt needle. For buccal dosing in dogs, a buccal patch or tablet was placed between the cheek and gum after moistening the dog's mouth with water. The mouth was held shut for 8 minutes to allow the tablet or patch to completely dissolve.

Plasma was collected and frozen until analysis of drug concentration. The area under the plasma concentration versus time curve (AUC) was calculated for each animal. Bioavailability was estimated by:

$$F = \frac{AUC_{(PO,B)} \times \text{Dose(IV)}}{AUC(\text{IV}) \times \text{Dose}_{(PO,B)}} \times 100\%$$

F represents the percentage of the administered dose absorbed into plasma. Bioavailability results are shown in Table 7. Buccal bioavailability data reflect the bioavailability of the parent compound after buccal administration of the specified prodrug. Administration of the 3-hydroxymorphinans buccally resulted in increased bioavailability relative to oral administration. Prodrugs of 3-hydroxymorphinans administered buccally also provided bioavailability much greater than oral bioavailability, and the claimed ester prodrugs have the advantage of being devoid of bitter taste.

TABLE 1

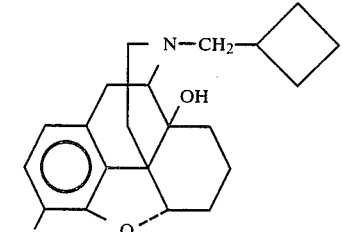

(Nalbuphine, R = H)

| | Hydrolysis Rate (t₁) | | |
| R | Rat Plasma | Human Plasma | Taste |
|---|---|---|---|
| H— (HCl salt) | NA | NA | bitter |
| H— (free base) | NA | NA | bitter |
| CH₃(CH₂)₁₀C(O)— | — | 0.9 hr. | none |
| (CH₃)₃C—C(O)— | 12 min. | <10% in 24 hr. | none |
| (CH₃CH₂)₃C—C(O)— (HCl salt) | <10% in 24 hr. | <10% in 24 hr. | none |
| o-CH₃-C₆H₄-C(O)— | — | 10% in 24 hr. | none |
| o-NH₂-C₆H₄-C(O)— | 1.5 hr. | 45 hr. | none |
| o-(OC(O)CH₃)-C₆H₄-C(O)— | 10 min. | 6.2 hr. | none |
| CH₃—S(O)₂— | 42 min. | 15.9 hr. | none |

TABLE 1-continued

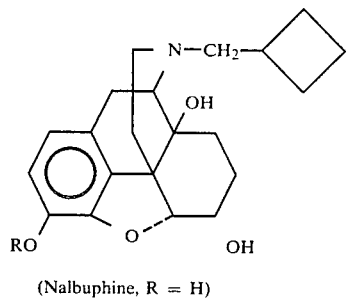

(Nalbuphine, R = H)

| | Hydrolysis Rate (t₁) | | |
| R | Rat Plasma | Human Plasma | Taste |
|---|---|---|---|
| CH₃—O—C(O)— | — | 0.5 hr. | not bitter* at first |
| CH₃O—C(O)—C₆H₄—NH—C(O)— (HCl salt) | — | 2.1 hr. | None |

*bitter taste develops due to hydrolysis in mouth

TABLE 2

NALOXONE (R = H)

| R | Salt | Taste |
|---|---|---|
| —H | HCl | bitter |
| —C(O)—C(CH₃)₃ | — | none |
| —C(O)—O—CH₂—C₆H₅ | — | none |
| —C(O)—CH₃ | — | none |
| —C(O)—C₆H₄—NH₂ | HCl | none |

TABLE 3

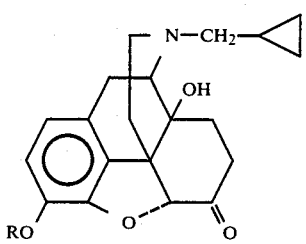

NALTREXONE (R = H)

| R | Salt | Taste |
|---|---|---|
| H | HCl | bitter |
| —C(=O)—C(CH$_3$) | — | none |

TABLE 4

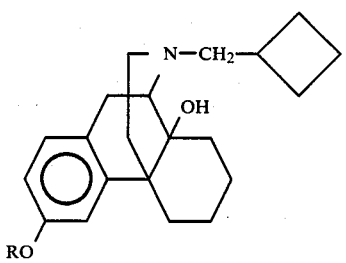

BUTORPHANOL (R = H)

| R | Salt | Taste |
|---|---|---|
| —H | tartrate | bitter |
| —C(=O)—C(CH$_3$)$_3$ | — | none |

TABLE 5

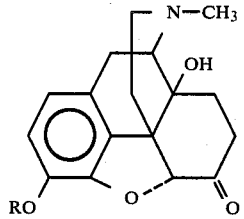

OXYMORPHONE (R = H)

| R | Salt | Taste |
|---|---|---|
| —H | Salt | bitter |
| —C(=O)—C(CH$_3$)$_3$ | — | none |

TABLE 6

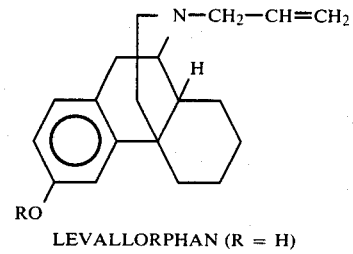

LEVALLORPHAN (R = H)

| R | Salt | Taste |
|---|---|---|
| —H | — | bitter |
| —C(=O)—C$_6$H$_4$—NH$_2$ | — | none |

TABLE 7
BIOAVAILABILITY RESULTS
(% dose: mean ± SD)

| | Rat | Dog |
|---|---|---|
| Oral Bioavailability | | |
| nalbuphine.HCl | 0.8 ± 0.4 | 5.3 ± 1.6 |
| naloxone.HCl | 0.3 ± 0.3 | — |
| naltrexone.HCl | 0.8 ± 0.7 | 1.0 ± 0.4 |
| Buccal Bioavailability[a] | | |
| naloxone.HCl | 76.7 ± 22.3 | — |
| naltrexone.HCl | 62.6 ± 12.1 | — |
| nalbuphine.HCl | 63.1 ± 22.5 | — |
| nalbuphine-3-pivalate.HCl | 45.5 ± 8.8 | 64.4 ± 15.6 |
| nalbuphine-3-acetylsalicylate | 86.9 ± 28.7[b] | 19.2[c] |
| nalbuphine-3-acetylsalicylate.HCl | — | 41.2 ± 3.4 |
| nalbuphine-3-salicylate[d] | 94.5 ± 34.0 | — |
| naloxone-3-pivalate.HCl | 61.9 ± 8.2 | 31.3 ± 7.3 |
| naltrexone-3-pivalate.HCl | 52.2 ± 14.8 | — |

[a]bioavailability of parent compound
[b]dissolved in 2.9% citric acid solution
[c]average of two dogs
[d]dissolved in 0.03 N.HCl "Consisting essentially of" in the present disclosure is intended to have its customary meaning; namely, that all specified material and conditions are very important in practicing the invention but that unspecified materials and conditions are not excluded so long as they do not prevent the benefits of the invention from being realized.

What is claimed is:

1. A pharmaceutical composition consisting essentially of (i) a therapeutically effective amount of a 3-hydroxymorphinan analgesic, agonist-antagonist, or narcotic antagonist of the formula:

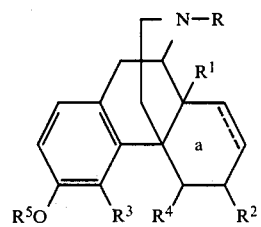

(I)

-continued

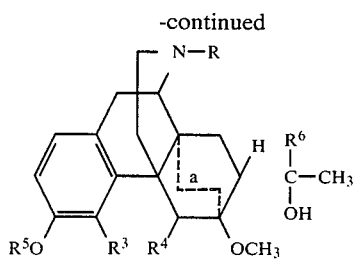

or a pharmaceutically acceptable acid addition salt thereof, wherein:

a is a single bond, or double bond;
R is methyl, allyl, methylallyl, cyclopropylmethyl, or cyclobutylmethyl;
$R^1$ is H, or OH;
$R^2$ is H, OH, =O, or =CH$_2$;
$R^3$ and $R^4$ are hydrogen, or taken together are —O—;
$R^5$ is alkanoyl of 2-18 carbon atoms; alkenoyl of 2-18 carbon atoms; mono- or dialkylcarbamoyl where each alkyl group contains 1-18 carbon atoms; alkylsulfonyl of 1-18 carbon atoms; alkylcarbonates where the alkyl group contains 1-18 carbon atoms; benzoyl, phenylsulfonyl; phenylcarbamoyl; substituted benzoyl; where the benzene ring contains 1-2 substituents individually selected from alkyl of 1-12 carbon atoms, $OR^7$, $NHR^7$ and $NR^7R^8$, Cl, F, Br, I, trifluoromethyl; substituted phenylsulfonyl or phenylcarbamoyl, where the benzene ring contains 1-2 substituents individually selected from alkyl of 1-12 carbon atoms, alkoxy of 1-12 carbon atoms, Cl, F, Br, I, $CF_3$;
$R^6$ is t-butyl or n-propyl;
$R^7$ is H, alkyl of 1-4 carbon atoms or $COR^9$;
$R^8$ is alkyl of 1-4 carbon atoms or $COR^9$; and
$R^9$ is H, or alkyl of 1-4 carbon atoms;

and (ii) a pharmaceutically acceptable carrier suitable for buccal, nasal, or sublingual administration.

2. A pharmaceutical composition according to claim 1, wherein the 3-hydroxymorphinan analgesic, agonist-antagonist, or narcotic antagonist is selected from the group consisting of nalbuphine, naltrexone, naloxone, nalmefene, morphine, butorphanol, oxymorphone, hydromorphone, levorphanol, levallorphan, buprenorphine, and etorphine.

3. A pharmaceutical composition according to claim 2, wherein the 3-hydroxymorphinan agonist-antagonist or narcotic antagonist is nalbuphine, naltrexone, or naloxone.

4. A pharmaceutical composition according to claim 1, wherein the carrier for buccal administration of the 3-hydroxymorphinan consists essentially of hydroxypropyl cellulose, carboxypolymethylene and polyethylene glycol.

5. A method of treating pain, controlling appetite, or reversing the effects of a narcotic drug in a mammal requiring such treatment, comprising administering to the mammal buccally, nasally, or sublingually a therapeutically effective amount of a pharmaceutical composition of claim 1.

6. A method of treating pain, controlling appetite, or reversing the effects of a narcotic drug in a mammal requiring such treatment, comprising administering to the mammal buccally, nasally, or sublingually a therapeutically effective amount of a pharmaceutical composition of claim 2.

7. A method of treating pain, controlling appetite, or reversing the effects of a narcotic drug in a mammal requiring such treatment, comprising administering to the mammal buccally, nasally, or sublingually a therapeutically effective amount of a pharmaceutical composition of claim 3.

8. A method of treating pain, controlling appetite, or reversing the effects of a narcotic drug in a mammal requiring such treatment, comprising administering buccally a pharmaceutical composition of claim 4.

* * * * *

UNITED STATES PATENT AND TRADEMARK OFFICE
CERTIFICATE OF CORRECTION

PATENT NO. : 4,673,679

DATED : June 16, 1987

INVENTOR(S) : Bruce J. Aungst/Munir A. Hussain

It is certified that error appears in the above-identified patent and that said Letters Patent is hereby corrected as shown below:

Structure (II) in Column 3, lines 2-10 and Column 15, lines 2-10 should be amended as follows:

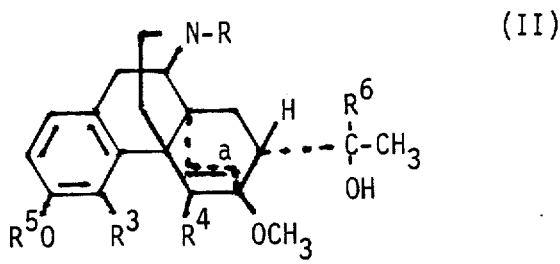

Signed and Sealed this

Twenty-seventh Day of October, 1987

Attest:

DONALD J. QUIGG

Attesting Officer

Commissioner of Patents and Trademarks